(12) United States Patent (10) Patent No.: US 7,589,210 B2
Tordo et al. (45) Date of Patent: Sep. 15, 2009

(54) NITRONS CARRYING A POSITIVE CHARGE AND USABLE IN TRAPPING FREE RADICALS, ESPECIALLY THE SUPEROXIDE RADICAL

(75) Inventors: Paul Tordo, Marseille (FR); Jean-Pierre Bernard Finet, Raphele les Arles (FR); Florence Nathalie Laurence Chalier, Marseille (FR); Olivier Ouari, Marseille (FR); Micael Hardy, La Seyne sur Mer (FR)

(73) Assignees: Universite de Provence (FR); Centre National de la Recherche Scientifique (CNRS) (FR)

( * ) Notice: Subject to any disclaimer, the term of this patent is extended or adjusted under 35 U.S.C. 154(b) by 248 days.

(21) Appl. No.: 11/585,731

(22) Filed: Oct. 24, 2006

(65) Prior Publication Data

US 2008/0009636 A1   Jan. 10, 2008

(30) Foreign Application Priority Data

Jul. 7, 2006 (FR) ................................. 06 06237

(51) Int. Cl.
*C07F 9/28* (2006.01)
(52) U.S. Cl. ..................................................... 548/111
(58) Field of Classification Search .................. 548/111
See application file for complete search history.

(56) References Cited

U.S. PATENT DOCUMENTS 5,354,871 A   10/1994   Arya et al.
5,750,710 A    5/1998   Frejaville et al.

FOREIGN PATENT DOCUMENTS

FR     2707990 B1    10/1995

OTHER PUBLICATIONS

Nitrones and Oxaziridines Bromination of 2-t-Butyl-and 2-Phenyl-1-pyrroline 1-Oxides, David St. C. Black and Neil A. Blackman, Aust. J. Chem. 1979; vol. 32, pp. 1795-1803.
ISR; PCT/FR2007/001157; Oct. 15, 2007.

*Primary Examiner*—Rei-tsang Shiao
(74) *Attorney, Agent, or Firm*—Lackenbach Siegel, LLP

(57) ABSTRACT

The present invention involves new nitrons carrying a positive charge, useful in trapping of free radicals and especially the superoxide radical, of general formula:

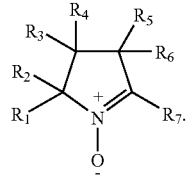

5 Claims, 7 Drawing Sheets

Figure 1. Curve of decline in the adducts Mito-DEPMPO/OOH and DEPMPO/OOH generated by the enzyme system hypoxanthine/xanthine oxidase at pH 7

Figure 2. Curve of decline in the adducts Mito-DEPMPO/OH and DEPMPO/OH generated by the enzyme system hypoxanthine/xanthine oxidase followed by the addition of SOD and of glutathione and of glutathione peroxidase at pH 7

Figure 3. Spectra obtained during the trapping of various free radicals by Mito-DEPMPO.

Figure 4. Spectra obtained during the trapping of various free radicals by 4HMDEPMPO.

Figure 5. Spectra obtained during the trapping of superoxide and hydroxyl radicals by 4HM-DEPMPO.

Figure 6. Spectra obtained during the trapping of superoxide and hydroxyl radicals by 4SCMDEPMPO.

Figure 7. Spectra obtained during the trapping of various free radicals by 4SCMDEPMPO.

NITRONS CARRYING A POSITIVE CHARGE AND USABLE IN TRAPPING FREE RADICALS, ESPECIALLY THE SUPEROXIDE RADICAL

PRIOR RELATED APPLICATION

This application claims priority from French Patent Application 06/06237, filed Jul. 7, 2006, and incorporates the prior application herein in its entirety.

BACKGROUND OF THE INVENTION

This application claims priority to French Patent Application 06 06237, filed Jul. 7, 2006, in its entirety and by reference thereto.

FIELD OF THE INVENTION

The present invention concerns molecules, in particular, new nitrons carrying a positive charge, for the trapping of free radicals, and especially for the trapping of the superoxide anion radical, as well as a method for preparing them.

Under the action of many intracellular processes, oxygen brought into the organism by respiration can be reduced to form various reactive oxygenated species, prooxidants such as the superoxide radical ($O2^{\cdot-}$), the hydroxyl radical ($HO^{\cdot}$), and the perhydroxyl radical ($HOO^{\cdot}$). In a normal situation, these species are eliminated by reaction with enzymatic or nonenzymatic antioxidizing substances, such as catalase, superoxide dismutase, glutathione peroxidase, glutathione, vitamin E or ascorbate, so that the concentration of reactive oxygenated species remains low in biological environments.

However, a disruption may occur in the equilibrium between the prooxidants and the antioxidants, leading to a situation of oxidative stress. These prooxidants, being highly unstable and present in excess amount, can then react nonselectively with a large number of compounds present in the cellular environment, such as amino acids, proteins, carbohydrates, the bases of DNA, as well as organic acids, especially lipids, which are unsaturated fatty acids. This may result in the inactivation of numerous enzymes, as well as modifications in regard to the permeability and fluidity of the cell membranes.

Thus, free radicals and especially the superoxide anion radical are implicated in many physiological and pathological situations in animals and man, such as coronary ischemia, arteriosclerosis, infarction, neurodegenerative diseases, numerous inflammatory, infectious, and aging processes. Very often the superoxide radical is the primary radical in the radical chain reaction in the organism. Its detection, its quantification and the determination of its production site are consequently important factors in the developing of therapeutic treatments.

It is thus important to be able to propose molecules acting as effective free radical traps, that is, ones which have a sufficiently considerable reactivity to compete with the other cell components, especially the superoxide radical.

The oxygenated radicals are species of very short lifetime. They cannot be isolated and detected directly. One of the strategies used at present to study these radicals is to combine the radical trapping technique with paramagnetic electron resonance (EPR). The principle of this radical trapping is to trap the radical on a diamagnetic molecule to yield a paramagnetic species, one which is persistent and can be detected by EPR.

The trap needs to be stable and nontoxic under the conditions of the experiment, it should interact selectively with the target free radicals, and their values of trapping speed should be elevated. The radical adducts resulting from the trapping should be sufficiently persistent to be observed by EPR and should possess EPR parameters characteristic of the trapped radical. The radicals having at least these properties and thus being used most often belong to two families of compounds:

the nitroso compounds $R_1N=O$ the nitrous

With these two families of molecules, the capture of a free radical results in an adduct of nitroxide type, which in the great majority of cases is persistent and observable by EPR. However, the nitroso compounds have major intrinsic difficulties, which limit their uses in aqueous environments. They are toxic, not very soluble in water, and have poor thermal or photochemical stability. What is more, the trapping of oxygenated radicals by nitroso derivatives results in adducts of very low persistence, quickly leading to products of molecular rearrangement. Consequently, the EPR spectra obtained during an experiment with radical trapping in presence of a nitroso derivative often correspond to the superpositioning of the signals of several nitroxides and are difficult to interpret.

The trap molecules most often used to trap radicals resulting from oxygen are the nitrons PBN a-phenyl-N-tert-butyl nitron) and DMPO (5,5-dimethyl-1-pyrroline-N-oxide).

PBN                DMPO

Recent works have shown that PBN and certain of its derivatives have a protector effect with regard to neuron death resulting from ischemia-reperfusion in the cerebral region. This protector therapeutic effect is attributed to a good cellular penetration of PBN, which can thus compete with the other cell components to react with the oxygenated radicals. Unfortunately, PBN does not constitute a trap of interest to the radical trapping technique, because of the very low persistence of its oxygenated adducts and their not very characteristic EPR parameters. Although its intracellular distribution is less than that of PBN, DMPO performs better in this regard, since it forms more persistent adducts with oxygen-centered radicals, which are more easy to detect and characterize. Even so, the use of DMPO to detect and characterize oxygen-centered radicals also has serious limits. For example, the adduct DMPO-OOH obtained with the superoxide radical has a half-life of only 60 seconds at physiological pH. On the other hand, the adduct DMPO-OOH breaks down partially into the adduct DMPO-OH, thus causing difficulties in the analysis of the mechanisms involved in the formation of the trapped radicals.

Other compounds are also known, such as 1' α-(4-pyridyl-1-oxide-N-tertbutyl nitron (POBN) and 2-methyl-2-nitrosopropane (MNP).

BACKGROUND AND DISCUSSION OF THE PRIOR ART

From patent EP 0 660 841 one is also aware of cyclical nitrons comprising, in particular, a phosphorylated compound, such as 2-diethylphosphono-2-methylpyrroline-N-oxide (DEPMO), resulting in trapping adducts relatively more stable than those obtained with the already known nitron derivatives.

However, in view of the stability of the adducts obtained with such compounds, a need still exists to propose molecules having superior performance to that of these already existing compounds, in particular, ones having an even more improved stability of the resulting adducts.

In particular, the superoxide radical has a very short lifetime in biological environments, which means that the existing rates of molecule trapping are too low to enable a detection of the molecules. Thus, one of the goals of the invention is to propose a trap molecule for free radicals and in particular for the superoxide radical that has an improved trapping rate, especially for the superoxide radical, and a greater stability for the adduct formed with said superoxide radical.

Toward this end, the object of the invention is compounds derived from cyclical nitrous of general formula.

in which R1 represents a phenyl, a (C6-C12) aryl or a (C1-C18) alkyl,

R2 represents an atom of hydrogen, of deuterium, a phenyl group, a (C6-C18) aryl group, a (C1-C1-C18) alkyl group, or a radical Z1 of formula in which A1 is a single bond, a methylene group, or an oxymethylene group (where the oxygen atom is bound to the phosphorus atom of the radical Z1), X represents an atom of oxygen or of sulfur, Y represents an atom of oxygen and R represents an atom of hydrogen, a (C1-C18) alkyl group or a (C6-C18) aryl group or Y represents a methylene group and R represents an atom of hydrogen, a (C1-C17) alkyl or a (C6-C18) aryl, or a radical Z3 of formula in which R represents an atom of hydrogen, a (C1-C18) alkyl or a (C6-C18) aryl group, R3 and R5 represent, independently, an atom of hydrogen, of deuterium, a phenyl, (C6-C18) aryl, or (C1-C18) alkyl group,

R4 represents a radical of formula in which X is a (C1-C18) alkyl or (C6-C18) aryl, A2 is an atom of oxygen, of nitrogen, or of carbon and Z is a positively charged group, such as a triaryl phosphonium $-P^+(Ar)_3$, Ar being a (C6-C18) aryl group, guanidinium $-NH-C(=NH)NH_3^+$, ammonium $-N^+(R)_3$, sulfonium $S^+(R)_2$, in which R is a group chosen from among the (C1-C18) alkyl and (C6-C18) aryl groups, substituted or not, saturated or not, possibly containing at least one atom of oxygen, nitrogen, and sulfur, R6 is an atom of hydrogen, of deuterium, a phenyl, (C6-C18) aryl, (C1-C18) alkyl group, or a radical Z2 of formula in which A2 is a single bond, a methylene group, or an oxymethylene group (where the oxygen atom is bound to the phosphorus atom of the radical Z2), X represents an atom of oxygen or of sulfur, Y represents an atom of oxygen and R represents an atom of hydrogen, a (C1-C18) alkyl or a (C6-C18) aryl, or Y represents a methylene group and R represents an atom of hydrogen, a (C1-C17) alkyl or (C6-C18) aryl, and R7 represents an atom of hydrogen, of deuterium, or a methyl group.

In very advantageous manner, it has been observed that the molecules according to the invention possess superior performance at trapping of free radicals and especially the superoxide radical, due to a long life for the adducts obtained and a trapping rate, especially for the superoxide radical, which is higher than that of the existing molecules, such as DMPO and DEPMPO, in particular thanks to the presence of the positive charge on the molecule of the invention, which attracts by electrostatic interaction the radicals being trapped, and carrying a negative charge, to the nitron radical.

Preferably, the compounds according to the invention correspond to the following general formula:

in which X is a (C1-C18) alkyl or (C6-C18) aryl,

A2 is an atom of oxygen, of nitrogen or of carbon and Z is a positively charged group, such as triaryl phosphonium $-P^+$

$(Ar)_3$, guanidinium $—NH—C(=NH)NH_3^+$, ammonium $—N^+(R)_3$, sulfonium $S^+(R)_2$, in which R is a group chosen from among the (C1-C18) alkyl and (C6-C18) aryl groups, substituted or not, saturated or not, possibly containing at least one atom of oxygen, nitrogen, and sulfur.

According to one preferred embodiment of the invention, the compound is the Mito-DEPMPO compound of formula:

SUMMARY OF THE INVENTION

The present invention also deals with precursor compounds, especially for trap compounds of the invention, of the following formula:

in which R1 represents a phenyl, a (C6-C18) aryl or a (C1-C18) alkyl,

R2 represents an atom of hydrogen, of deuterium, a phenyl group, a (C6-C18) aryl, (C1-C18) alkyl, or a radical Z1 of formula in which A1 is a single bond, a methylene group, or an oxymethylene group (where the oxygen atom is bound to the phosphorus atom of the radical Z1), X represents an atom of oxygen or of sulfur, Y represents an atom of oxygen and R represents an atom of hydrogen, a (C1-C18) alkyl or a (C6-C1-C18) aryl or Y represents a methylene group and R represents an atom of hydrogen, a (C1-C17) alkyl or (C6-C18) aryl, R3 and R5 represent, independently, an atom of hydrogen, of deuterium, a phenyl, (C6-C18) aryl, or (C1-C18) alkyl group, R4 represents a radical of formula R6 is an atom of hydrogen, of deuterium, a phenyl, (C6-C18) aryl, (C1-C18) alkyl group, or a radical Z2 of formula in which A2 is a single bond, a methylene group, or an oxymethylene group (where the oxygen atom is bound to the phosphorus atom of the radical Z2), X represents an atom of oxygen or of sulfur, Y represents an atom of oxygen and R represents an atom of hydrogen, a (C1-C18) alkyl or a (C6-C18) aryl, or Y represents a methylene group and R represents an atom of hydrogen, a (C1-C17) alkyl or (C6-C18) aryl, and R7 represents an atom of hydrogen, of deuterium, or a methyl group.

DESCRIPTION OF THE PREFERRED EMBODIMENTS

According to one preferred embodiment of the invention, the precursor compound is:

Such a free radical trap molecule carries a freely activated group which makes it possible to prepare new trap molecules by functionalization with ligands providing appropriate properties and thus leading to the preparation of bifunctional traps having superior trapping performance, such as when a cation group is introduced.

The present invention also deals with a method for preparation of the free radical trap compound that is preferable according to the invention, involving the synthesis of 4HMDEPMPO by the following synthesis pathway:

Then the carbonation of the nitron 5-diethoxyphosphoryl-5-methyl-4-hydroxymethyl-1-pyrroline N-oxide (4HMDEPMPO) thus obtained in solution in acetonitrile with succinimide carbonate and triethylamine The nitron thus formed is then caused to react with 1 equivalent of (2-aminoethyl)triphenyl phosphonium bromide in presence of triethylamine in dichloroethane, thereby producing the Mito-DEPMPO compound We shall now describe the following preparation examples which illustrate without limiting the invention.

Example of synthesis of 4-(1-diethoxyphosphoryl-1-nitroethyl)-tetrahydrofuran-2-one 2.16 g of tributylphosphane (0.01 mol) are added drop by drop to a mixture of nitrophosphate (12.58 g, 0.059 mol) and furanone (5 g, 0.059 mol) in 70 ml of cyclohexane. Methylene chloride (7 ml) is added to fully solubilize the reaction mixture, which is agitated for 24 h at ambient temperature. The solvent is evaporated tinder reduced pressure. The crude product is purified by flash chromatography on silica gel with the eluent being a mixture of Et2O/pentane (9/1). The nitrofuranone, in diastereoisomeric mixture (55/45), is obtained in the form of a pale yellow oil (14.01 g, 0.047 mol) with a yield of 80%.

$d_P$ (121.49 MHz; CDCl$_3$; H$_3$PO$_4$) 13.70 (55%), 13.79 (45%).

Remark: the 2 diastereoisomers have signals which are superposed or nonattributable in NMR $^1$H.

$d_H$ [see original]

| multiplicity of the carbons form of the signal (attribution) | d (in ppm) of the diastereoisomer of $d^{31}P$ = 13.70 ppm | d (in ppm) of the diastereoisomer of $d^{31}P$ = 13.70 ppm |
|---|---|---|
| 2 × 1C, s, (CO) | 174.48 | 174.63 |
| 2 × 1C, d, C$^{IV}$NO$_2$ | 90.09 ($J_{CP}$ = 147.1) | 90.42 ($J_{CP}$ = 148.2) |

| multiplicity of the carbons form of the signal (attribution) | d (in ppm) of the diastereoisomer of $d^{31}P = 13.70$ ppm | d (in ppm) of the diastereoisomer of $d^{31}P = 13.70$ ppm |
|---|---|---|
| 2 × 2C, d, CH$_2$OC(O) | 68.27 ($J_{CP}$ = 2.8) | 68.14 ($J_{CP}$ = 9.3) |
| 2 × 1C, d, 2CH$_2$OP | 64.80 ($J_{CP}$ = 7.7) | 65.05 ($J_{CP}$ = 7.2) |
| 2 × 1C, d, CHC$^{IV}$ | 40.20 | 39.75 |
| 2 × 1C, s, CH$_2$CO | 29.85 ($J_{CP}$ = 7.7) | 30.19 ($J_{CP}$ = 3.3) |
| 2 × 1C, d, CH$_3$C$^{IV}$ | 16.37 ($J_{CP}$ = 9.4) | 16.36 ($J_{CP}$ = 7.7) |
| 2 × 2C, d, CH$_3$CH$_2$O | 16.25 ($J_{CP}$ = 5.2) | 16.28 ($J_{CP}$ = 5.2) |

Elemental analysis for C10H18NO7P (molecular weight=295.23):
Calculated: C, 40.68; H, 6.15; N, 4.74%.
Found: C, 40.67; H, 6.07; N, 4.61%.

Example of synthesis of 2-hydroxy-4-(1-diethoxyphosphoryl-1-nitroethyl)-tetrahydrofurane:

To a solution of 1.3 g (4.4 mmol) of 4-(1-diethoxyphosphoryl-1-nitroethyl)-tetrahydrofuran-2-one in 35 ml of CH$_2$Cl$_2$ at −78° C. are added drop by drop 11.45 ml of a solution of DIBAL-H 1M in hexane. The reaction mixture is agitated for 3 h and then the mixture is hydrolyzed. The mixture is quickly filtered on silica gel, then dried on Na$_2$SO$_4$. The solvent is evaporated under reduced pressure. The crude product (1.4 g) is purified by flash chromatography on silica gel with the eluent being a mixture of CH$_2$Cl$_2$/Et$_2$O. The 4 diastereoisomers of the hemiacetal are obtained in mixture (650 mg, 2.19 mmol) in the form of a pale yellow oil with a yield of 50%.

$d_P$ (121.49 MHz; CDCl$_3$; H$_3$PO$_4$) 15.15 (50%), 15.28 (25%), 15.48 (25%).

Remark: the 4 diastereoisomers have signals which are superposed or nonattributable in NMR $^1$H.

$d_H$ [see original] [key: respectivement=respectively]
Elemental analysis for C10H20NO7P (297.24):
Calculated: C, 40.41; H, 6.78; N, 4.71%.
Found: C, 40.42; H, 6.65; N, 4.49%.

Example of synthesis of 5-diethoxyphosphoryl-5-methyl-4-hydroxymethyl-1-pyrroline N-oxide or 4HMDEPMPO:

4HMDEPMPOc      4HMDEPMPOt

To a solution of 3.8 g (0.128 mol) of hemiacetal 28 in a mixture of THF/H$_2$O (1/1) is added NH$_4$Cl (1.71 g, 0.032 mol) and then finely powdered zinc (2.00 g, 0.032 mol) is added. The reaction mixture is left under agitation for 6 h at ambient temperature. The precipitated ZnCl$_2$ is then eliminated by filtration and rinsed with CH$_2$Cl$_2$ (3×40 ml). The filtrate is then concentrated under reduced pressure and the residue is dissolved in 40 ml of CH$_2$Cl$_2$. The combined organic phases are dried on Na$_2$SO$_4$ and the solvent is evaporated under reduced pressure to yield 3 g of a yellow oil. The crude product is purified by flash chromatography on silica gel with the eluent being a mixture of CH$_2$Cl$_2$/EtOH (80/20) to give 3 fractions with a yield of 64%. Of the 3 fractions obtained, one being a hygroscopic red solid (1.22 g, 0.006 mol, 38% yield) corresponded to 4HMDEPMPOc (4S, 5R or 4R, 5S). Another one, being a red oil (630 mg, 0.0024, 19% yield), was composed entirely of 4HMDEPMPOt (4R, 5R or 4S, 5S). The stereochemistry of the two nitrons was confirmed by NOESY NMR.

Spectral characteristics of (4S*, 5R*)-4HMDEPMPOc:
$d_P$(121.49 MHz; CDCl$_3$p; H$_3$PO$_4$) 20.85.
$d_H$(300.13 MHz; CDCl$_3$; Me$_4$Si) 6.92 (1H, q, $J_{HH}$=$J_{HP}$=2.7, HC=N), 4.39-4.14 (4H, m, CH$_3$CH$_2$OP), 3.90 (2H, d, $J_{HH}$=6.1, CH$_2$OH), 2.78-2.39 (4H, m, CHCH$_2$OH, CH$_2$C=NO, OH), 1.76 (3H, d, $J_{HP}$=14.5, CH$_3$C$^{IV}$NO), 1.38 (3H, t, $J_{HH}$=7.0, CH$_3$CH$_2$OP), 1.34 (3H, t, $J_{HH}$=7.0, CH$_3$CH$_2$OP).

$d_C$(75.47 MHz; CDCl$_3$; Me$_4$Si) 134.52 (1C, d, $J_{CP}$=8.8, HC=N), 76.93 (1C$^{IV}$, d, $J_{CP}$=149.8, CH$_3$C$^{IV}$), 63.86 (1C, d, $J_{CP}$=7.1, CH$_3$CH$_2$OP), 63.81 (1C, d, $J_{CP}$=7.7, CH$_3$CH$_2$OP), 62.23 (1C, d, $J_{CP}$5.0, CH$_2$OH), 49.32 (1C, d, $J_{CP}$=2.8, CH$_2$C=), 29.16 (1C, s, CHCH$_2$OH), 21.31 (1C, d, $J_{CP}$=1.6, CH$_3$C$^{IV}$), 16.40 (1C, d, $J_{CP}$=5.5, CH$_3$CH$_2$OP), 16.25 (1C, d, $J_{CP}$=6.0 CH$_3$CH$_2$OP).

Pf. 48° C. (decomposition).

Spectral characteristics of (4R*, 5R*)-4HMDEPMPOt:
$d_P$(121.49 MHz; CDCl$_3$; H$_3$PO$_4$) 22.0.
$d_H$(300.13 MHz; CDCl$_3$; Me$_4$Si) 6.85 (H$_v$, q, $J_{HH}$=$J_{HP}$=2.5, HC=N), 4.40-4.11 (4H, m, CH$_3$CH$_2$O), 3.82 (Ha, ABd, $J_{HaHb}$=11.0 & $J_{HaHc}$=7.0, CH$_2$OH), 3.66 (Hb, ABd, $J_{HbHa}$=11.0 & $J_{HbHc}$=5.9, CH$_2$OH), 3.25-3.05 (H$_c$, m, CHCH$_2$OH), 2.87 (H$_d$, ABdt, $J_{HdHe}$=18.3 & $J_{HdHe}$=6.6 & $J_{HdHv}$=$J_{HdP}$=2.5 CHC=NO), 2.48 (1H & H$_e$, ABtd, $J_{HeHd}$=18.3, $J_{HeHe}$=6.6, $J_{HeP}$=6.6, $J_{HeHv}$=2.5, CHC=NO, OH), 1.67 (3H, d, $J_{HP}$=16.0, CH$_3$C$^{IV}$NO), 1.34 (3H, t, $J_{HH}$=6.9, CH$_3$CH$_2$OP), 1.33 (3H, t, $J_{HH}$=6.9, CH$_3$CH$_2$OP). $d_C$(75.47 MHz; CDCl$_3$; Me$_4$Si) 134.87 (1C, d, $J_{CP}$=8.8 HC=N), 76.74 (1C$^{IV}$, d, $J_{CP}$=158.1, CH$_3$C$^{IV}$), 64.08 (1C, d, $J_{CP}$=6.6 CH$_3$CH$_2$OP), 63.25 (1C, d, $J_{CP}$=7.3, CH$_2$OH), 61.26 (1C, d, $J_{CP}$=6.6, CH$_2$OP), 40.85 (1C, s, CHCH$_2$OH), 30.14 (1C, d, $J_{CP}$=4.8, CH$_2$C=N) 16.24 (2C, $J_{CP}$=5.9 CH$_3$CH$_2$OP), 14.01 (1C, s, CH$_3$C$^{IV}$), Elemental analysis for C$_{10}$H$_{20}$NO7P+½ of H2O (274.25) of the two diastereoisomers:
Calculated: C, 43.80; H, 7.72; N, 5.11%.
Found: C, 44.06; H, 7.60; N, 5.33%.

ESI-MS/MS [see original, data]

Example of synthesis of (4R*, 5S*)-5-diethoxyphosphoryl-4-(succinimidyloxycarbonyloxymethyl)-5-methyl-1-pyrroline-N-oxide:

To a solution of 0.234 g of disuccinimide carbonate (0.91 mmol) in acetonitrile (5 ml) is added 0.1 ml of triethylamine (0.76 mmol) and 0.202 g of nitron (0.76 mmol). The reaction mixture is left under agitation for 16 h. It is then concentrated under reduced pressure. It is dissolved in dichlormethane and then washed with a saturated solution of $NaHCO_3$ until pH=8, then with a saturated solution of NaCl. The organic phase is dried on $Na_2SO_4$ and the solvent is evaporated to yield 220 mg of a yellow oil. The crude product is purified by flash chromatography on silica gel with the eluent being a mixture of $CH_2Cl_2$/EtOH (90/10) to give 4SCMDEPMPOc (170 mg, 0.419 mmol) in the form of a white powder with a yield of 55%.

Spectral characteristics of the nitron (4S*, 5R*):
$d_P$(81.01 MHz; $CDCl_3$; $H_3PO_4$) 18.0.
$d_H$(200.13 MHz; $CDCl_3$; $Me_4Si$) 6.97 ($H_v$, q, $J_{HH}=J_{HP}=2.9$, HC=N), 4.76 (1H, ABd, $J_{HAHB}=10.8$ & $J_{HAH}=5.9$, $\underline{CH_2}$OCO), 4.57 (1H, ABd, $J_{HBHA}=10.8$ & $J_{HBH}=7.8$, $\underline{CH_2}$OCO), 4.36-4.08 (4H, m, $CH_3\underline{CH_2}$O), 2.83 (4H, s, $\underline{CH_2}$CO), 2.8-2.57 (3H, m, $\underline{CH}CH_2$O, $\underline{CH_2}$C=NO), 1.71 (3H, d, $J_{HP}=13.9$, $CH_3C^{IV}$NO), 1.31 (3H, t, $J_{HH}=7.0$, $\underline{CH_3}CH_2$OP), 1.33 (3H, t, $J_{HH}=7.0$, $\underline{CH_3}CH_2$OP).
$d_C$(50.32 MHz; $CDCl_3$; $Me_4Si$) 168.44 (2C, s, CON), 151.10 (1C, s, COO), 133.73 (1C, d, $J_{CP}=7.7$ HC=N), 75.86 ($1C^{IV}$, d, $J_{CP}=148.7$, $CH_3\underline{C}^{IV}$), 70.00 (1C, d, $J_{CP}=3.0$, $\underline{CH_2}$OCO), 64.51 (1C, d, $J_{CP}=6.5$, $\underline{CH_2}$OP), 62.80 (1C, d, $J_{CP}=7.2$, $\underline{CH_2}$OP), 45.45 (1C, d, $J_{CP}=2.3$, $\underline{CH}CH_2$O), 29.68 (1C, d, $J_{CP}=0.8$, $\underline{CH_2}$C=N), 25.28 (2C, s, $\underline{CH_2}$CO), 20.1 (1C, s, $CH_3C^{IV}$), 16.13 (2C, d, $J_{CP}=5.7$, $\underline{CH_3CH_2}$OP).
Pf. 81.4° C. décomposition.
Exact mass for C15H23N2O9P, [C15H23N2O9P+Na]$^+$.
Calculated: 429.1039.
Found: 429.1062.

Example of synthesis of the trap molecule according to the invention.

To a mixture of 4-NHSDEPMPO (0.5 g, 1.23 mmol) and (2-aminoethyl)triphenylphosphonium bromide (0.48 g, 1.24 mmol) in solution in $CH_2Cl_2$ (30 ml) is added triethylamine (0.23 mL, 1.61 mmol) at ambient temperature. The mixture is agitated for 2 hours, then washed with 15 ml of water. The organic phase is dried on $Na_2SO_4$ and the solvent is eliminated under reduced pressure. The product is purified on a silica column ($CH_2Cl_2$/EtOH 70.30) to give a white solid (0.57 g, 69%) corresponding to 4-MitoDEPMPO.
$^{31}$P NMR (121.49 MHz) d 20.13, 21.52. $^1$H NMR (300.13 MHz) d 7.89 (1H, t, J=6.1), 7.76-7.60 (15H, m), 6.88 (1H, q, J=2.4), 4.34-4.01 (6H, m), 3.92-3.76 (2H, m), 3.64-3.52 (2H, m), 2.65-2.45 (3H, m) 1.60 (3H, d, J=14.1), 1.28 (3H, t, J=7.0), 1.24 (3H, t, J=6.9). $^{13}$C NMR (75.47 MHz) d 156.4 ($1C^{IV}$, s), 135.1 (3C, d, J=2.9), 134.8 (1C, d, J=8.0), 133.5 (6C, d, J=10.3), 130.4 (6C, d, J=13.2), 122.7 (3C, d, J=86.1), 75.8 (1C, d, J=149.2), 64.1 (2C, d, J=6.3), 62.5 (1C, d, J=7.5), 46.3 (1C, d, J=2.3), 35.0 (1C, s), 30.5 (1C, s), 23.0 (1C, d, J=48.7), 20.1 (1C, s), 16.3 (1C, d, J=5.7), 16.2 (1C, 3d, J=5.7).
ESI-MS/MS (60 eV) m/z 597.0 [M+H]$^+$ (100), 378.3 (20.1), 350.0 (9.3), 332.2 (22.6), 306.3 (1.0), 288.9 (7.9), 277.2 (0.6), 275.3 (0.4), 262.9 (0.4), 262.0 (0.6), 248.0 (0.6), 220.0 (2.5), 174.0 (2.7), 155.7 (0.6), 115.9 (0.2), 110.2 (0.4), 107.9 (0.2), 94.0 (0.7), 88.0 (0.7).
HRMS calculated for [C31H39N2O6P2]+, Br$^-$; [C31H39N2O6P2]+597.2253, found: 597.2283.

BRIEF DESCRIPTION OF THE DRAWINGS

The invention shall now be described in further detail by means of the following figures, in which.

Figure 1:
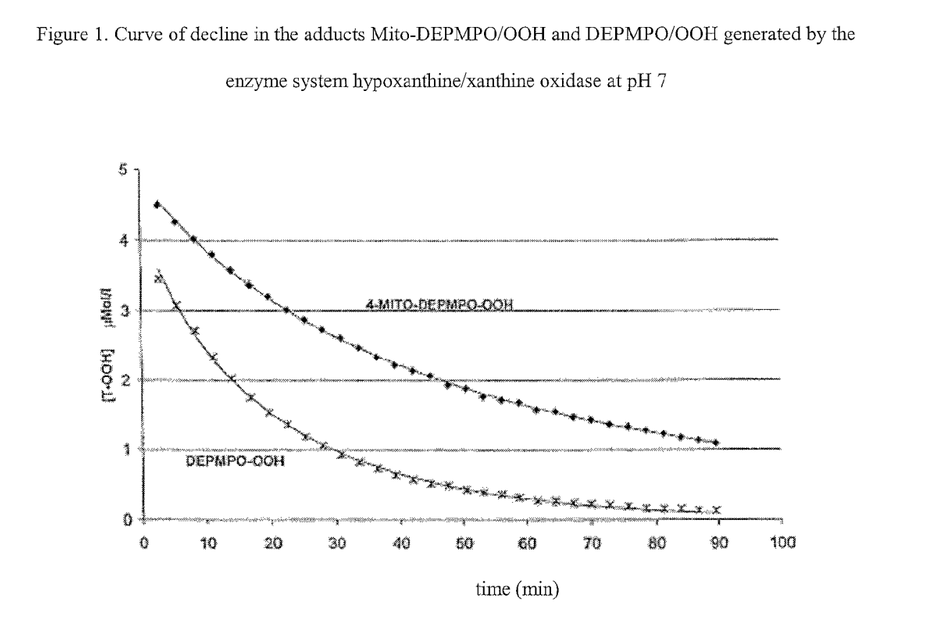
FIG. 1 shows the decay curves obtained for adducts obtained with a molecule according to the invention and a method of the prior art (DEPMPO)

As can be seen in FIG. 1, the decay curve for the Mito-DEPMPO/OOH adducts generated by the enzyme system hypoxanthine/xanthine oxidase at pH 7 reveals that the half-life of these adducts is quite better than that of the DEPMPO/OOH adducts generated by the enzyme system hypoxanthine/xanthine oxidase at pH 7.

Figure 2:
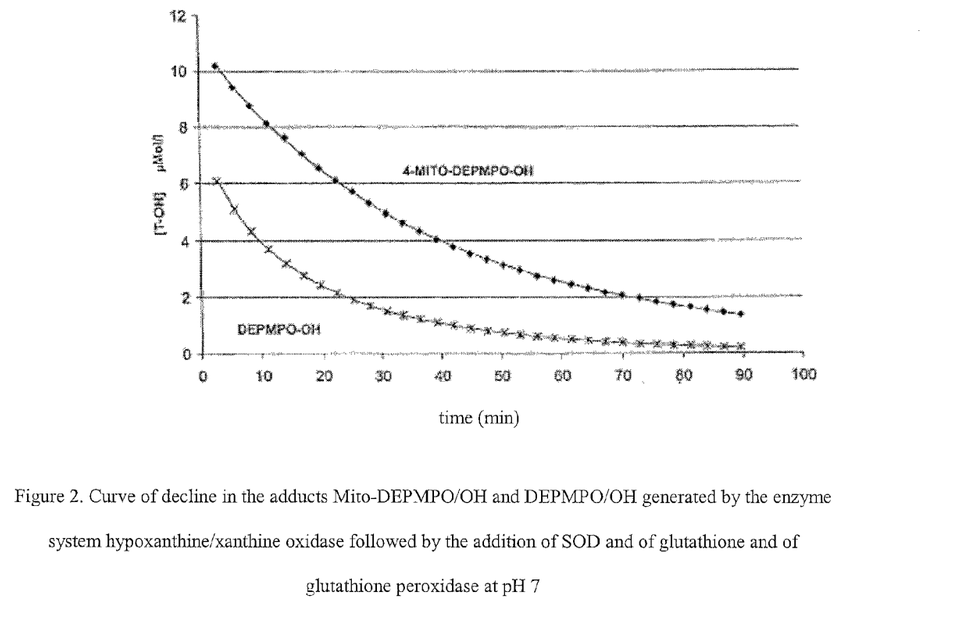
FIG. 2 shows the decay curves obtained for adducts obtained with a molecule according to the invention and a method of the prior art (DEPMPO)

Likewise, FIG. 2, decay curve for the Mito-DEPMPO/OH adducts generated by the enzyme system hypoxanthine/xanthine oxidase followed by the addition of SOD and of glutathione and of glutathione peroxidase at pH 7 reveals that the half-life of these adducts is quite better than that of the DEPMPO/OH adducts.

Figure 3:
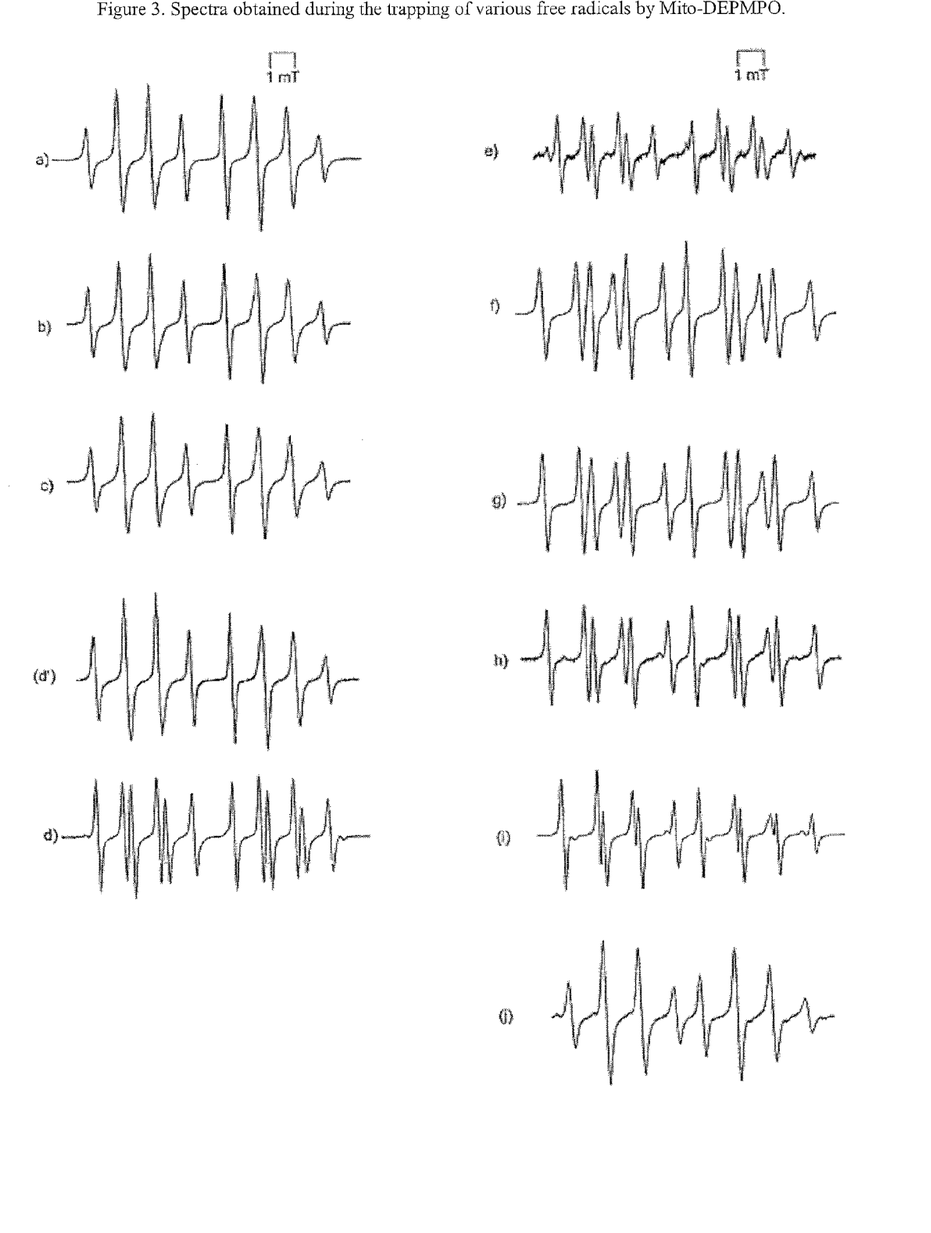
FIG. 3 shows spectra obtained from the trapping of various free radicals with a molecule of the prior art (DEPMPO)

In FIG. 3 are shown spectra obtained by electron paramagnetic resonance (EPR) from the trapping of various free radicals by mito-DEPMPO, as follows:

(a) Signal obtained (Mito-DEPMPO/OOH) after 10 min. of incubation of a mixture containing hypoxanthine (HX) (0.4 mM), xanthine oxidase (XO) (0.04 U/mL), DTPA (1 mM) and Mito-DEPMPO (20 mM) in a phosphate buffer (0.1 M, pH 7.3).
(b) Like (a), but after 60 min.
(c) Signal obtained after 2 min of incubation of a mixture containing the system KO2/18-c-6 crown ether (10 mM) and Mito-DEPMPO (20 mM) in a phosphate buffer (0.1 M, pH 7.3).
(d') like (a), with 0.2 G of amplitude modulation.
(d) Signal obtained 10 min. after reduction of the superoxide adduct obtained in (a) with GPX (10 U/mL)+GSH (1.2 mM) followed by 3 min. of argon bubbling.
(e) Signal obtained after 1 min. incubation of a mixture containing Mito-DEPMPO (20 mM), $H_2O_2$ (2 mM), Fe2SO4 (2 mM), DTPA (1 mM) in a phosphate buffer (0.1 M, pH 7.3).
(f) like (e), but in presence of 5% of EtOH after 30 min.
(g) Like (e), but in presence of 7% of MeOH after 30 min.

(h) like (e), but in presence of 10% of DMSO after 30 min. and argon bubbling.
(i) like (e) but in presence of 7% of HCOOH.
(j) Signal obtained after 10 min. of photolysis of a mixture containing Mito-DEPMPO (20 mM), GSNO (1 mM), DTPA (1 mM) and a phosphate buffer (0.1 M, pH 7.3). Spectrometer adjustment: wave power 10 mW (a-c, e-j), 20 mW (d); amplitude modulation, 0.2 (d'), 0.5 (a, e, f-i), 0.63 (j), 0.7 (b), 0.8 (d-e); time constant, 0.640 ms (a-c, d', e-f, i), 1.28 ms (d, h, j); gain $10^5$ (a-j); sweep time, 335.54 s (a-c, e-j), 167.77 (d); conversion time 0.163 s (a-c, e-j), 0.082 s (d), 0.327 s (d').

Figure 4:
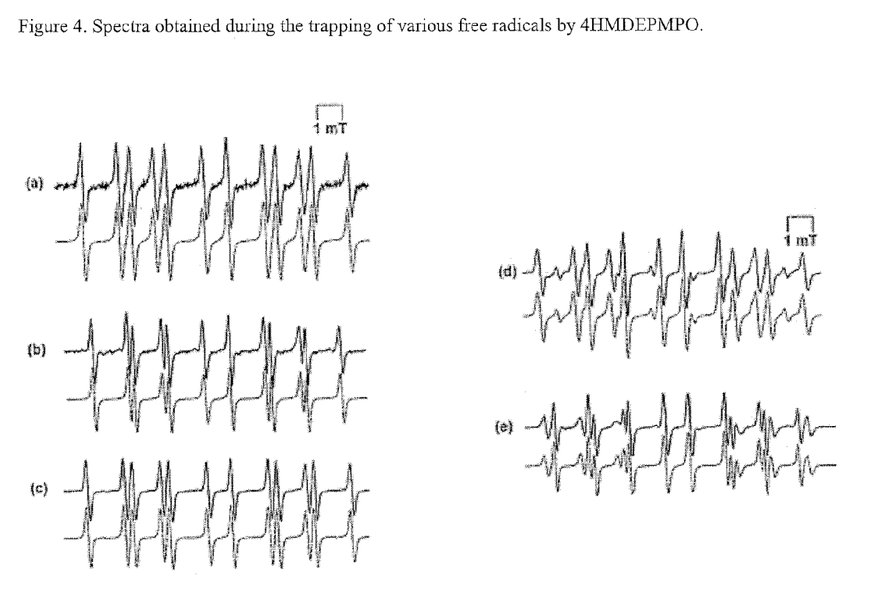
FIG. 4 shows spectra obtained from the trapping of various free radicals with 4HMDEPMPO.

FIG. 4 shows spectra (EPR) obtained from the trapping of various free radicals with 4-HMDEPMPO, as follows:
(a) signal obtained 34 min. after the production of hydroxyl radicals by the system (H2O2, 2 mM, FeSO4, 2 mM) in a phosphate buffer (0.1 M, pH 7.3) in presence of MeOH (10%), 4HMDEPMPOc (61 mM) and DTPA (1 mM).
(b) like (a) after 1 min. incubation in presence of HCOOH (10%).
(c) like (a) after 10 min. incubation in presence of DMSO (5%) in an argon purged environment.
(d) like (a) after 1 min. incubation in presence of EtOH (10%) and 4HMDEPMPOc (50 mM).
(e) like (d) after 1 min. incubation in presence of CH3COH (10%). The signals shown gray represent the spectra simulated by the program ROKI. Registration conditions: power, 10 mW (a-e); amplitude modulation, 0.0991 (b), 0.497 (a, c, e), 0.702 (d); time constant, 1.28 ms (a-e); gain, $10^5$ (a-e); sweep time, 84 s (a-e); conversion time 82 ms (a-e).

Figure 5:
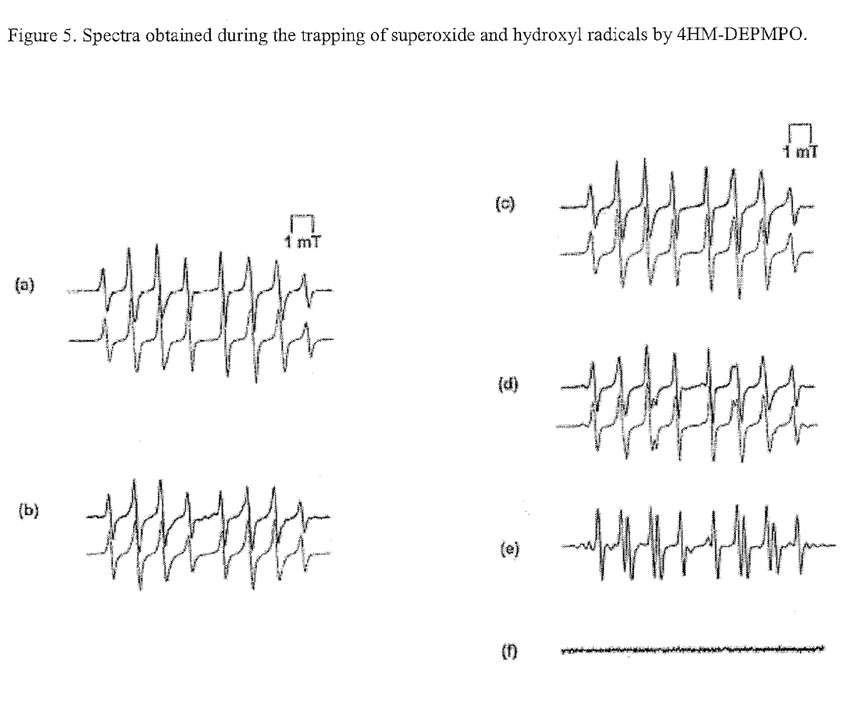
FIG. 5 shows spectra obtained from the trapping of superoxide and hydroxyl free radicals with 4HMDEPMPO.

FIG. 5 shows spectra (EPR) obtained from the trapping of the superoxide and hydroxyl radicals with 4HM-DEPMPO, as follows:
(a) signal obtained 34 min. after the production of hydroxyl radicals by the system (H2O2, 2 mM, FeSO4, 2 mM) in phosphate buffer (0.1 M, pH 7.3) in presence of MeOH (10%), 4HMDEPMPOc (61 mM) and DTPA (1 mM).
(b) like (a) after 1 min. incubation in presence of HCOOH (10%).
(c) like (a) after 10 min. incubation in presence of DMSO (5%) in an argon purged environment.
(d) like (a) after 1 min. incubation in presence of EtOH (10%) and 4HMDEPMPOc (50 mM).
(e) like (d) after 1 min. incubation in presence of CH3COH (10%).

The signals shown gray represent the spectra simulated by the program ROKI. Registration conditions: power, 10 mW (a-e); amplitude modulation, 0.0991 (b), 0.497 (a, c, e), 0.702 (d); time constant, 1.28 ms (a-e); gain, $10^5$ (a-e); sweep time, 84 s (a-e); conversion time 82 ms (a-e).

Figure 6:
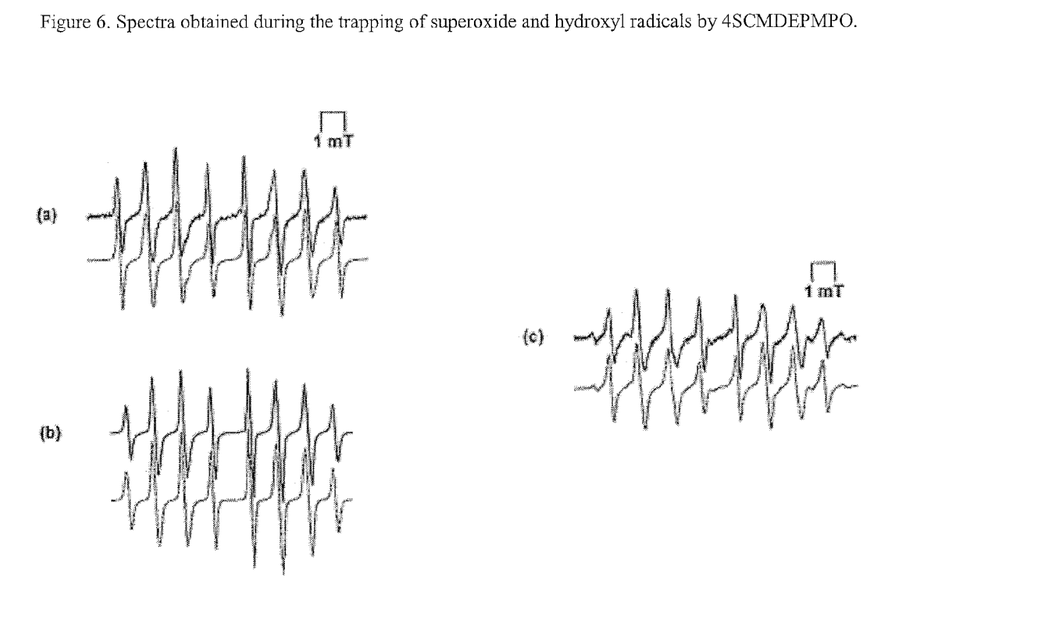
FIG. 6 shows spectra obtained from the trapping of various free radicals with 4SCMDEPMPO.

FIG. 6 shows spectra (EPR) obtained from the trapping of the superoxide and hydroxyl radicals with 4SCMDEPMPO, as follows:
(a) signal 1 min. after the liberation of superoxide radicals by KO2 (5 mM) in a phosphate buffer (0.1 M, pH 7.3) in presence of 4SCMDEPMPOc (50 mM).
(b) 2 min. after photolysis of tert-butylhydroperoxide (1.5 M) in presence of 4SCMDEPMPOc (20 mM) in a degassed mixture (9/1) of toluene/$CH_2Cl_2$.
(c) 1 min. after production of methylperoxyl radicals by the Fenton system (H2O2, 2 mM, FeSO4, 2 mM) in a phosphate buffer (0.1 M, pH 7.3) saturated with O2 in presence of DMSO (5%), 4SCMDEPMPOc (10 mM) and DTPA (1 mM).

The signals shown gray represent the spectra simulated by the program ROKI. Registration conditions: power, 10 mW (a-c); amplitude modulation, 0.056 (b), 0.497 (c), 0.702 (a); time constant, 0.320 ms (b), 1.28 ms (a, c); gain, $3.2 \times 10^4$ (b) $10^5$ (a, c); sweep time, 335.54 s (b), 84 s (a, c); conversion time 327.68 ms (b), 82 ms (a, c).

Figure 7:
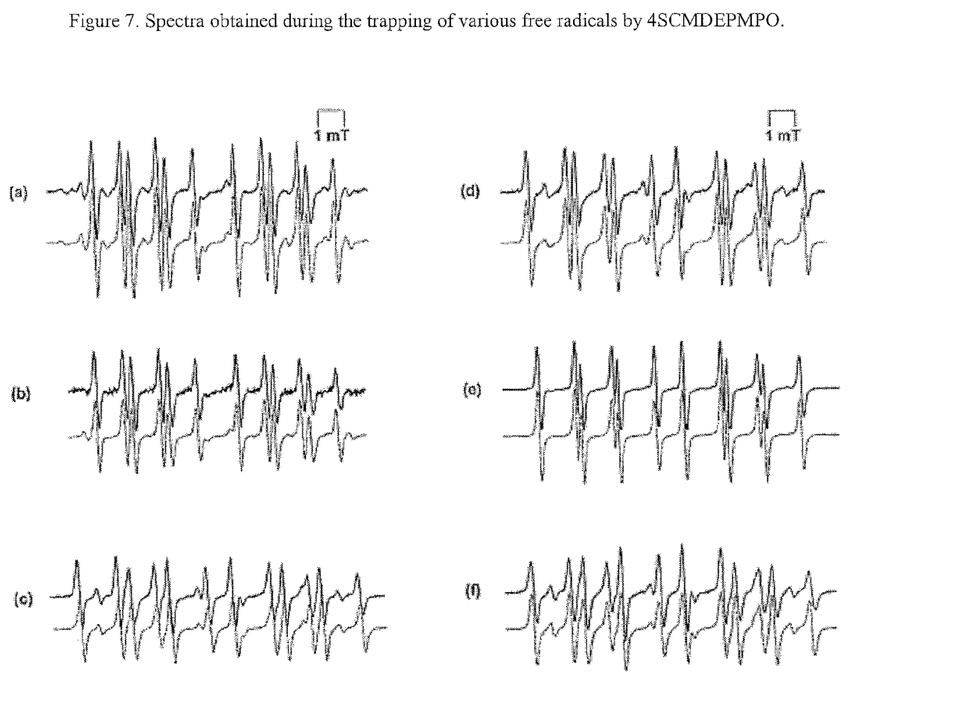
FIG. 7 shows spectra obtained from the trapping of various free radicals with 4SCMDEPMPO.

FIG. 7 shows spectra (EPR) obtained from the trapping of various free radicals with 4SCMDEPMPO, as follows:
(a) signal obtained 1 min. after the production of hydroxyl radicals by the system (H2O2, 2 mM, FeSO4, 2 mM) in a phosphate buffer (0.1 M, pH 7.3) in presence of 4SCM-DEPMPOc (20 mM) and DTPA (1 mM).
(b) like (a) after 5 min. incubation.
(c) like (a) after 1 min. incubation in presence of MeOH (2%) and 4SCMDEPMPOc (20 mM).
(d) like (a) after 1 min. incubation in presence of DMSO (5%) in an argon purged environment in presence of 4SCMDEP-MPOc (20 mM).
(e) like (d) after 1 min. incubation in presence of HCOOH (1%) and 4SCMDEPMPOc (20 mM).
(f) like (a) after 1 min. incubation in presence of EtOH (2%) and 4SCMDEPMPOc (20 mM). The signals shown gray represent the spectra simulated by the program ROKI. Registration conditions: power, 10 mW (a-f); amplitude modulation, 0.497 (a-f); time constant, 1.28 ms (a-f); gain, $10^5$ (a-f); sweep time, 84 s (a-f); conversion time 82 ms (a-f).

What is claimed is:
1. A compound of the general formula:

in which R1 represents a phenyl, a (C1-C18) aryl, a (C1-C18) alkyl,
R2 represents an atom of hydrogen, of deuterium, a phenyl group, a (C1-C18) aryl, (C1-C18) alkyl, or a radical Z1 of formula in which A1 is a single bond, a methylene group, or an oxymethylene group, where the oxygen atom is bound to the phosphorus atom of the radical Z1, X represents an atom of oxygen or of sulfur, Y represents an atom of oxygen and R represents an atom of hydrogen, a (C1-C18) alkyl or a (C6-C18) aryl, Y represents a methylene group and R represents an atom of hydrogen, a (C1-C17) alkyl, a (C6-C18) aryl,
or a radical Z3 of formula in which R represents an atom of hydrogen, a (C1-C17) alkyl, a (C6-C18) aryl group R3 and R5 represent, independently, an atom of hydrogen, of deuterium, a phenyl, (C1-C18) aryl, an (C1-C18) alkyl group,

R4 represents a radical of formula in which X is a (C1-C18) alkyl or (C6-C18) aryl, A2 is an atom of oxygen, of nitrogen, or of carbon and Z is a positively charged group and selected from a triaryl phosphonium —P$^+$(Ar)$_3$, Ar being a (C6-C18) aryl group, guanidinium —NH—C(=NH)NH$_3{}^+$, ammonium —N$^+$(R)$_3$, sulfonium S$^+$(R)$_2$, in which R is a group chosen from among the (C1-C18) alkyl and (C6-C18) aryl groups, substituted or not, saturated or not, possibly containing at least one atom of oxygen, nitrogen, and sulfur,

R6 is an atom of hydrogen, of deuterium, a phenyl, (C1-C18) aryl, (C1-C18) alkyl group, a radical Z2 of formula in which A2 is a single bond, a methylene group, an oxymethylene group, where the oxygen atom is bound to the phosphorus atom of the radical Z2, X represents an atom of oxygen or of sulfur, Y represents an atom of oxygen and R represents an atom of hydrogen, a (C1-C18) alkyl, a (C6-C18) aryl, Y represents a methylene group and R represents an atom of hydrogen, a (C1-C17) alkyl, (C6-C18) aryl, and R7 represents an atom of hydrogen, of deuterium, a methyl group.

2. The compound according to claim 1 of the formula:

in which X is a (C1-C18) alkyl, a (C6-C18) aryl,

A2 is an atom of oxygen, of nitrogen or of carbon and Z is a positively charged group, and selected from a triaryl phosphonium —P$^+$(Ar)$_3$, guanidinium —NH—C(=NH)NH$_3{}^+$, ammonium —N$^+$(R)$_3$, sulfonium S$^+$(R)$_2$, in which R is a group chosen from among the (C1-C18) alkyl and (C6-C18) aryl groups, substituted or not, saturated or not, possibly containing at least one atom of oxygen, nitrogen, and sulfur.

3. The compound according to claim 2, of the formula:

4. A compound of the formula:

in which R1 represents a phenyl, a (C1-C18) aryl, a (C$_1$-C18) alkyl,

R2 represents an atom of hydrogen, of deuterium, a phenyl group, a (C1-C18) aryl, (C1-C18) alkyl, a radical Z1 of formula in which A1 is a single bond, a methylene group, an oxymethylene group, where the oxygen atom is bound to the phosphorus atom of the radical Z1, X represents an atom of oxygen, of sulfur, Y represents an atom of oxygen and R represents an atom of hydrogen, a (C1-C18) alkyl or a (C6-C18) aryl or Y represents a methylene group and R represents an atom of hydrogen, a (C1-C17) alkyl or (C6-C18) aryl, R3 and R5 represent, independently, an atom of hydrogen, of deuterium, a phenyl, (C1-C18) aryl, a (C1-C18) alkyl group, R4 represents a radical of formula

R6 is an atom of hydrogen, of deuterium, a phenyl, (C1-C18) aryl, (C1-C18) alkyl group, a radical Z2 of formula in which A2 is a single bond, a methylene group, an oxymethylene group, where the oxygen atom is bound to the phosphorus atom of the radical Z2, X represents an atom of oxygen or of sulfur, Y represents an atom of oxygen and R represents an atom of hydrogen, a (C1-C18) alkyl or a (C6-C18) aryl, or Y represents a methylene group and R represents an atom of hydrogen, a (C1-C17) alkyl, (C6-C18) aryl, and R7 represents an atom of hydrogen, of deuterium, a methyl group.

5. The compound according to claim 4, of the formula:

* * * * *